(12) United States Patent
Ishibiki et al.

(10) Patent No.: US 6,855,108 B2
(45) Date of Patent: Feb. 15, 2005

(54) ENDOSCOPE HOOD MEMBER AND ENDOSCOPE SYSTEM

(75) Inventors: Kota Ishibiki, Hachioji (JP); Hiroki Moriyama, Akishima (JP)

(73) Assignee: Olympus Corporation (JP)

( * ) Notice: Subject to any disclaimer, the term of this patent is extended or adjusted under 35 U.S.C. 154(b) by 105 days.

(21) Appl. No.: 10/253,667

(22) Filed: Sep. 24, 2002

(65) Prior Publication Data

US 2003/0088154 A1 May 8, 2003

(30) Foreign Application Priority Data

Sep. 25, 2001 (JP) ........................................ 2001-292360
Oct. 18, 2001 (JP) ........................................ 2001-321137

(51) Int. Cl.[7] .................................................. A61B 1/00
(52) U.S. Cl. ........................ 600/127; 600/121; 600/129
(58) Field of Search ................................ 600/121, 127, 600/129, 160, 163, 171, 172, 173, 175, 176

(56) References Cited

U.S. PATENT DOCUMENTS 5,897,487 A  *  4/1999  Ouchi ........................ 600/127

FOREIGN PATENT DOCUMENTS

| JP | 57-136430 | 8/1982 |
| JP | 11-206702 | 8/1999 |
| JP | 11-313795 | 11/1999 |
| JP | P-2000-180735 A | 6/2000 |
| JP | 2001-224550 | 8/2001 |

OTHER PUBLICATIONS

Office Action from Japanese Patent Office dated Aug. 14, 2003 relating to Application No. 2001-292360.
English translation of Office Action from Japanese Patent Office dated Aug. 14, 2003 relating to Application No. 2001-292360.

* cited by examiner

*Primary Examiner*—Beverly M. Flanagan
(74) *Attorney, Agent, or Firm*—Ostrolenk, Faber, Gerb & Soffen, LLP

(57) ABSTRACT

It is provided an endoscope apparatus including an observing device that displays an observation view area. The observation view area is displayed on the observing device of this endoscope as a non-circular observed image. A hood member is mounted on an end of an inserted section of the endoscope and includes a hood section projecting in the direction of the observation view area. At least a part of the hood section is provided with a slope that is shaped so as to correspond to the observation view area.

35 Claims, 8 Drawing Sheets

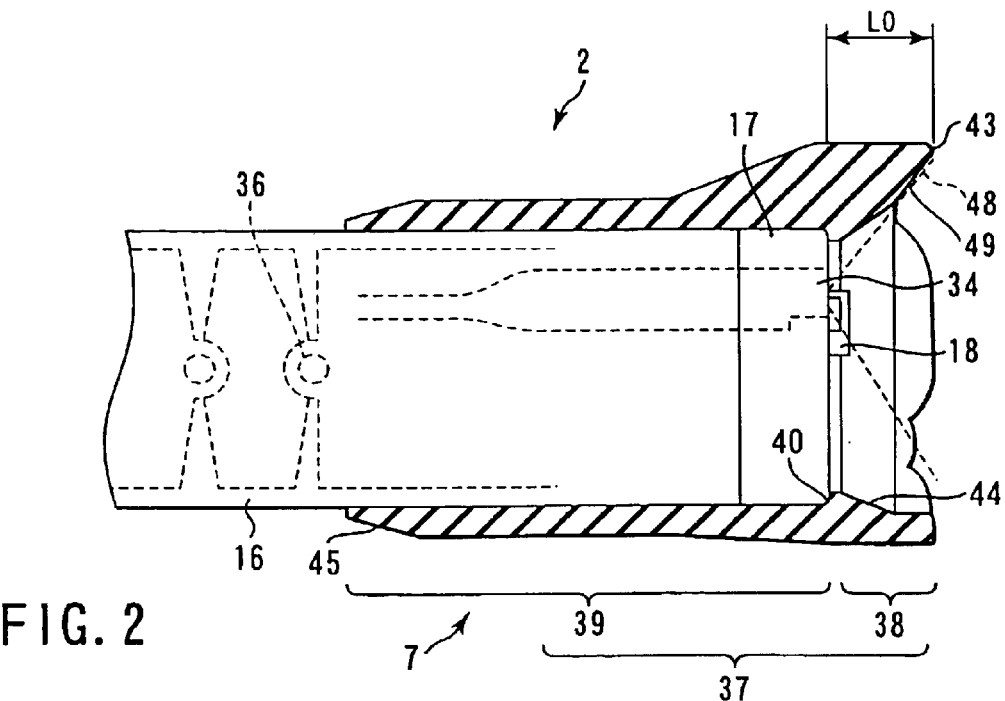
FIG. 2
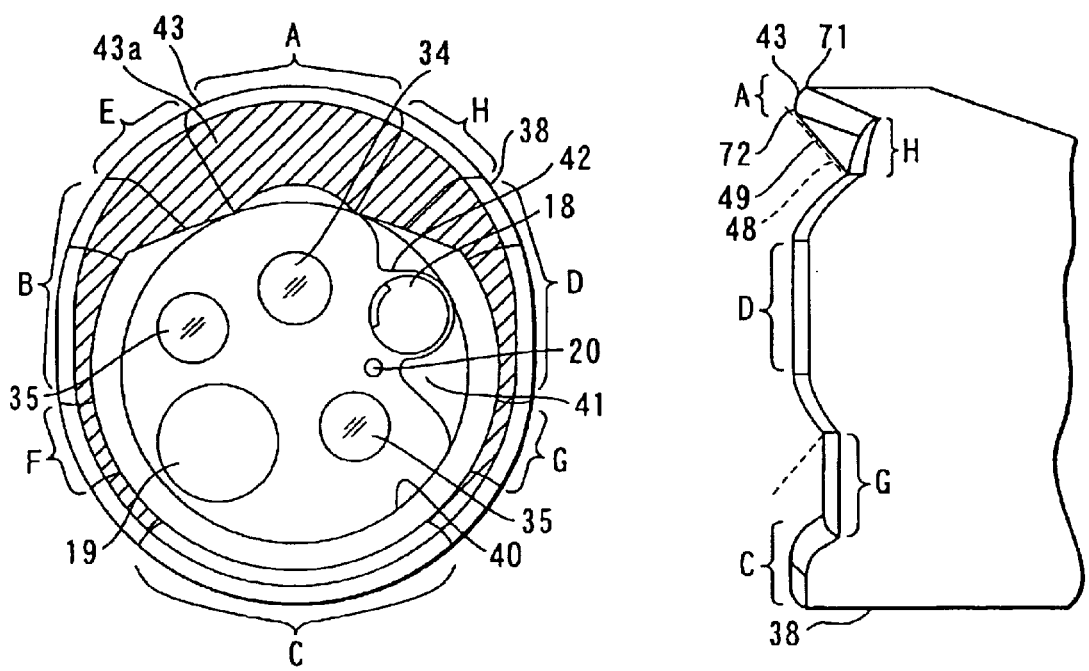
FIG. 3
FIG. 4

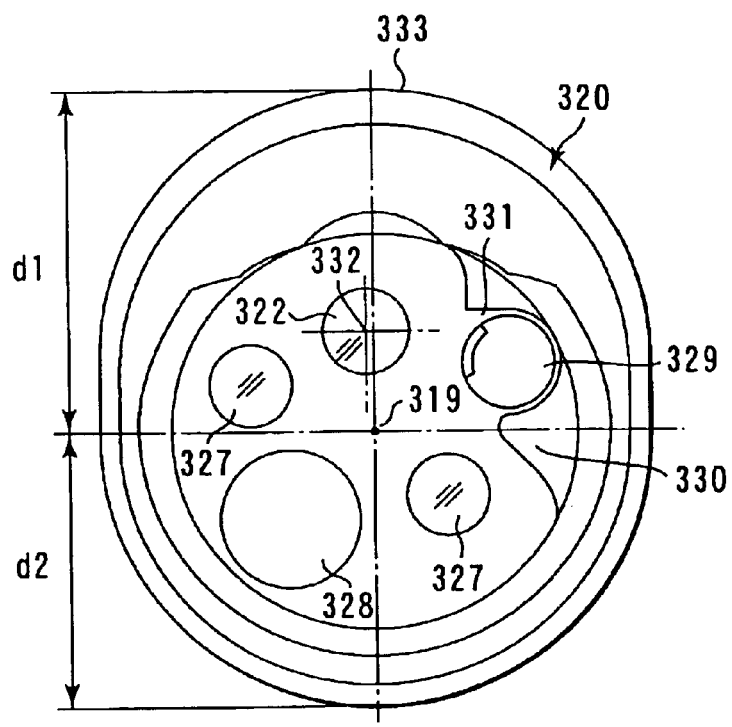
FIG. 19
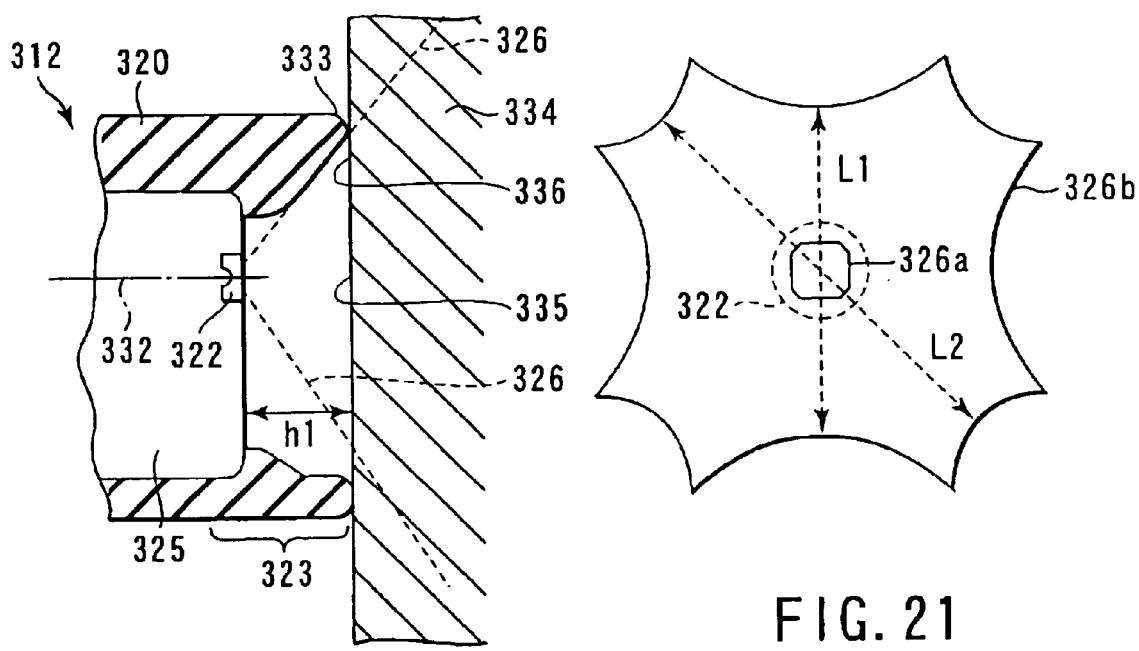
FIG. 20
FIG. 21

ENDOSCOPE HOOD MEMBER AND ENDOSCOPE SYSTEM

CROSS-REFERENCE TO RELATED APPLICATIONS

This application is based upon and claims the benefit of priority from the prior Japanese Patent Applications No. 2001-292360, filed Sep. 25, 2001; and No. 2001-321137, filed Oct. 18, 2001, the entire contents of which are incorporated herein by reference.

BACKGROUND OF THE INVENTION

1. Field of the Invention

The present invention relates to an endoscope apparatus having a hood member provided at an end portion of an inserted portion of an endoscope.

2. Description of the Related Art

A conventional example of an endoscope apparatus for use in an operation is formed by disposing an objective lens, a light guide, an air and water supply port, and a suction port in an end portion of an inserted portion of an endoscope. Such an endoscope apparatus irradiates a subject such as living tissue with light from the light guide and allows the lighted subject to be viewed via the objective lens so as to suck, through the suction port, air, water, or other substances fed through the air and water supply port.

In this regard, when an attempt is made to insert the endoscope into, for example, the stomach, the mucous membrane of the stomach often contacts with and covers the objective lens provided in the end portion of the inserted portion of the endoscope. Thus, more inner areas of the stomach can no longer be viewed.

Correspondingly, Jpn. Pat. Appln. KOKAI Publication No. 11-206702 discloses an end structure of an endoscope in which the end portion of the inserted portion of the endoscope is provided with a guide portion to prevent the mucous membrane from covering the objective lens and blocking the view. The guide portion of the end structure of the endoscope is a hood-like member having an inner peripheral surface gradually widened so as to draw a curve starting from an end surface of its end portion.

Jpn. Pat. Appln. KOKAI Publication No. 11-313795 discloses an endoscope in which a hood member is formed to have a thickness or projecting height varying depending on a view angle. Such an endoscope has a smaller thickness or projecting height in a direction in which the view angle is larger or at a position close to an observing optical system.

BRIEF SUMMARY OF THE INVENTION

It is an object of the present invention to provide a fitting jig of an endoscope hood member and an endoscope apparatus which provide an appropriate observation area.

According to a first aspect of the invention, there is provided an endoscope apparatus comprising: an endoscope apparatus comprising an observing device which has an observation view area, the observing device displaying the observation view area as a noncircular observed image; and a hood member mounted on an end of an inserted section and comprising a hood section which projects in the direction of the observation view area, at least a part of the hood member being provided with a slope that is shaped so as to correspond to the observation view area.

According to a second aspect of the invention, there is provided an endoscope apparatus comprising: an endoscope which has an inserted section provided with an objective optical system at an end of the inserted section, the objective optical system having an observation view area; an observed image display device which displays an image of the observation view area of the objective optical system as an observed image; and a hood member mounted on the end of the inserted section and having a hood section which extends in the direction of the observation view area, at least a part of the hood member being provided with a slope section that is shaped so as to correspond the observation view area.

According to a third aspect of the invention, there is provided an endoscope hood member comprising: a mounted section mounted on an end of an endoscope inserted section which includes an objective optical system having an optical axis offset from an axis of the endoscope inserted section; and a hood section, which is formed on the mounted section, the outer periphery of which projects further in a direction in which the optical axis of the objective optical system is arranged with respect to the axis of the endoscope inserted section, than in the other directions.

According to a fourth aspect of the invention, there is provided an endoscope apparatus comprising: an endoscope which includes an inserted section having an axis; an objective optical system provided in the inserted section and having an optical axis arranged offset from the axis of the inserted section; and a hood member provided on an end portion of the inserted section and having a mounted section and a hood section the outer periphery of which projects further in a direction in which the optical axis of the objective optical system is arranged with respect to the axis of the endoscope inserted section than in the other directions.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a sectional view of an end portion of the first embodiment in FIG. 1;

FIG. 3 is a front view of the end portion of the endoscope of the first embodiment in FIG. 1;

FIG. 4 is a side view showing a hood member removably connected to the end portion of the endoscope of the first embodiment in FIG. 1;

FIG. 19 is a front view of the end portion of the endoscope according to the fifth embodiment;

FIG. 20 is a view showing how the end portion of the endoscope according to the fifth embodiment abuts against a wall of a living body; and FIG. 21 is a view of an observation view area of the endoscope according to the fifth embodiment as viewed from the front of the apparatus.

DETAILED DESCRIPTION OF THE INVENTION

Embodiments of the present invention will be described below with reference to the drawings.

First Embodiment

Figure 1:
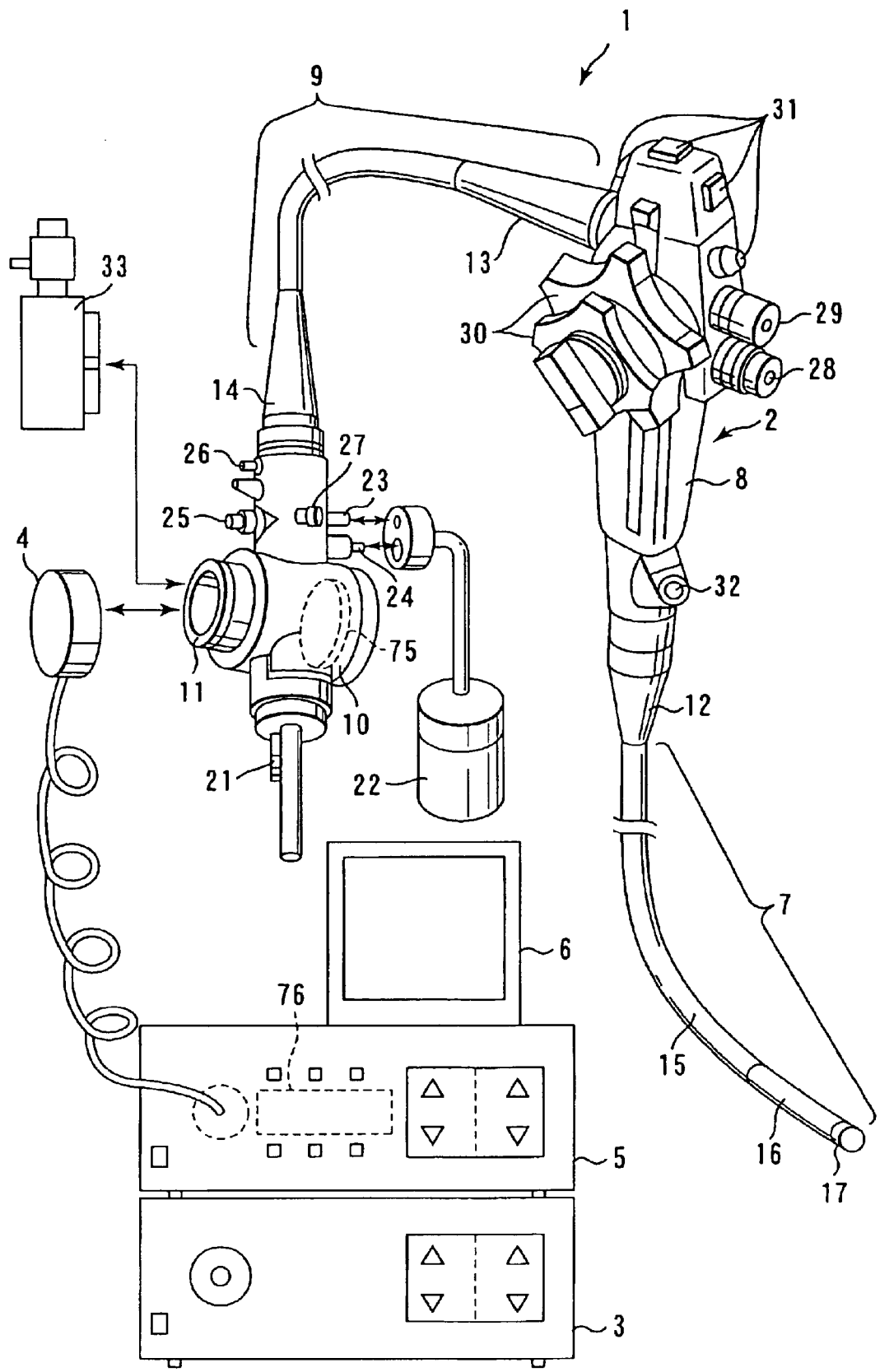
FIG. 1 is a view illustrating the entire configuration of an endoscope apparatus according to a first embodiment of the present invention.
Figure 5:
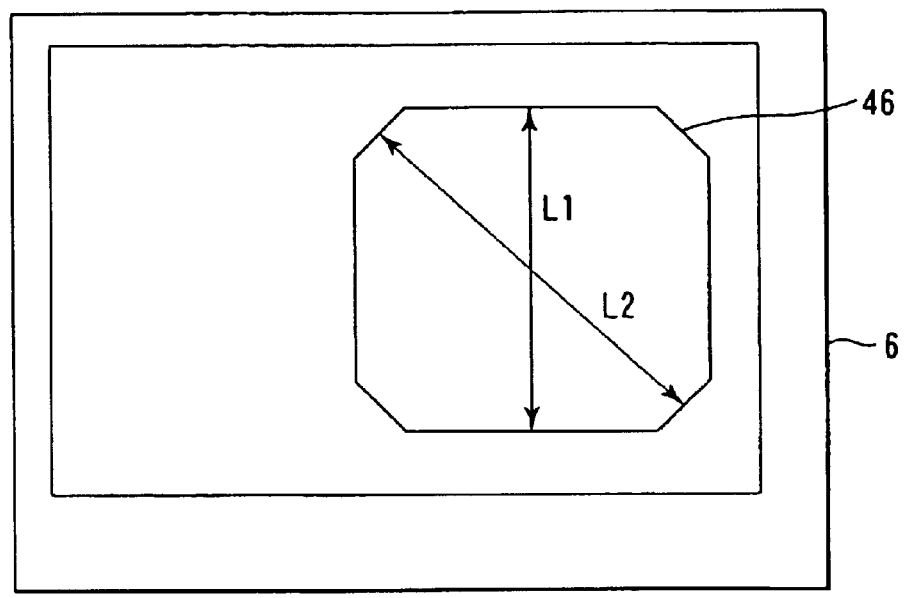
FIG. 5 is a plan view showing an observed image displayed on a monitor according to the first embodiment of the present invention.
Figure 6:
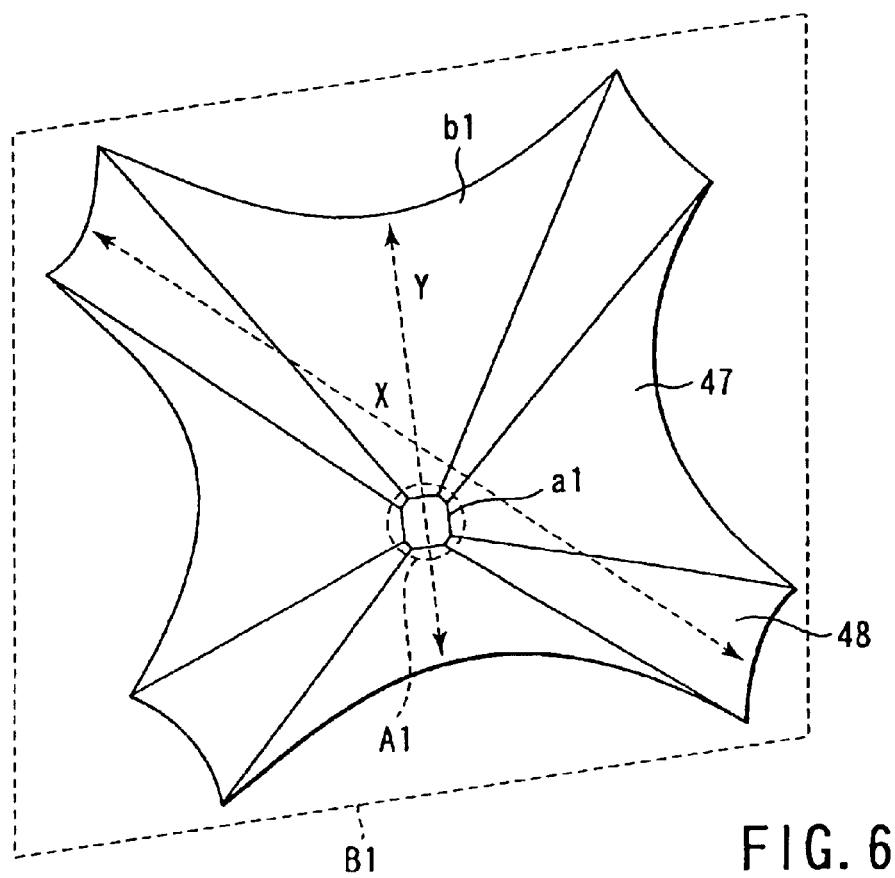
FIG. 6 is a view illustrating an observation view area used if the observed image in FIG. 5 is displayed.

FIGS. 1 to 6 relates to a first embodiment of the present invention. FIG. 1 is a view illustrating the entire configuration of an endoscope apparatus. FIG. 2 is a sectional view of an end portion of an endoscope. FIG. 3 is a front view of the end portion of the endoscope. FIG. 4 is a side view showing a hood member removably connected to the end portion of the endoscope. FIG. 5 is a plan view showing an observed image displayed on a monitor. FIG. 6 is a view illustrating an observing view area used if the observed image in FIG. 5 is displayed.

FIG. 1 shows the entire configuration of the endoscope apparatus.

As shown in FIG. 1, the endoscope apparatus 1 is composed of an endoscope 2, a light source device 3, a video processor 5, and a monitor 6.

The endoscope 2 comprises image pickup means described later. The light source device 3 is removably connected to the endoscope 2 to supply illumination light to a light guide formed in the endoscope 2. The video processor 5 is connected to the endoscope 2 via a signal cable 4 to control the image pickup means of the endoscope 2 and to process signals obtained from the image pickup means. The monitor 6 displays a video corresponding to an image of a subject output by the video processor 5.

The endoscope 2 has an inserted portion 7, a manipulating section 8, a connection cord 9, a connector section 10, and an electric connector section 11.

The inserted portion 7 is flexible and is formed to be elongated. The manipulating section 8 is connected to a proximal side of the inserted portion 7. The connection cord 9 is flexible and extends from a side of the manipulating section 8. The connector section 10 is provided at an end of the connection cord 9 and is adapted to be removably connected to the light source device 3. The electric connector section 11 is provided on a side of the connector section 10 so that the signal cable 4, connected to the video processor 5, can be removably connected to the electric connector section 11.

The electric connector section 11 is provided with a ventilation section (not shown) that allows the interior and exterior of the endoscope 2 to communicate with each other.

The connection between the inserted portion 7 and the manipulating section 8 is provided with an inserted-portion fold preventing member 12 having an elastic portion that prevents the connection from being sharply bent. The connection between the manipulating section 8 and the connection cord 9 is provided with a manipulating-section fold preventing member 13 similar to the inserted-portion fold preventing member 12. Furthermore, the connection between the connection cord 9 and the connector section 10 is provided with a connector-section fold preventing member 14 similar to the inserted-portion fold preventing member 12.

The inserted portion 7 is composed of a flexible tube portion 15, a bent portion 16, and an end portion 17 which are connected together in this order from the proximal end of the inserted portion.

The flexible tube portion 15 is formed so as to be flexible. The bent portion 16 is provided at the end of the flexible and can be bent while being manipulated by the manipulating section 8. An observing optical system, an illuminating optical system, and the like are disposed in the end portion 17; the optical systems are provided at the end of the inserted portion and will be described later.

As shown in FIGS. 2 and 3, the end portion 17 is provided with an air and water supply nozzle 18 as an air and water supply port, a suction port 19, a water supply port 20, an observing optical system 34, and an illuminating optical system 35.

The air and water supply nozzle 18 ejects a cleaning fluid or a gas to an optical member provided on an outer surface of the observing optical system 34. The suction port 19 is an opening located at the end of a treatment instrument channel through which a treatment instrument disposed in the inserted portion 7 is inserted or a liquid in the coelom is sucked. The water supply port 20 is open toward an object to be observed so that a liquid can be ejected to the object.

As shown in FIG. 1, the connector section 10 is provided with a gas supply cap 21, a water supply tank pressurizing cap 23, a water supply cap 24, a suction cap 25, an injection cap 26, and an earth terminal cap 27.

The gas supply cap 21 is removably connected to a gas supply source (not shown) built into the light source device.

The water supply tank pressurizing cap 23 and the water supply cap 24 are removably connected to the water supply tank 22 as a water supply source. The suction cap 25 is connected to a suction source (not shown) to suck a gas or liquid through the suction port 19, shown in FIG. 3. The injection cap 26 is connected to water supply means (not shown) to feed water through the water supply port 20, shown in FIG. 3. The earth terminal cap 27 returns, to a high-frequency processor, a high-frequency leakage current generated in the endoscope 2 because of a high-frequency treatment or the like.

The manipulating section 8 is provided with an air and water supplying operation button 28, a sucking operation button 29, a bending operation knob 30, a plurality of remote switches 31, and a treatment instrument insertion port 32.

The air and water supplying operation button 28 is an operation section used to perform an air or water supplying operation. An operator can depress this button to supply air or liquid through the air and water supply nozzle 18, shown in FIG. 3. The sucking operation button 29 is an operation section used to perform a sucking operation. The operator can depress this button to perform a sucking operation through the suction port 19, shown in FIG. 3. The bending operation knob 30 is an operation section used to bend the bent portion 16. The plurality of remote switches 31 constitute an operation section used to remotely operate the video processor 5. The operation instrument insertion port 32 is a proximate opening that is in communication with the treatment instrument channel.

Further, a waterproof cap 33 can be removably connected to the electric connector section 11 of the endoscope 2 to seal the electric connector section 11 in a liquid tight manner.

Now, a hood member 37, an essential part of the present invention, will be described.

As shown in FIGS. 2 and 3, the hood member 37 is removably connected to the end portion 17 of the inserted portion 7 of the endoscope 2.

That is, the hood member 37, while fixed to the end portion 17, prevents a tip lens of the observing optical system 34 from directly abutting against the inner wall of the coelom. The hood member 37 thus prevents the view of the endoscope 2 from being blocked.

The hood member 37 can be formed of a soft member such as vulcanized rubber such as silicon rubber or fluorine rubber, or a thermoplastic elastomer such as an urethane-based elastomer, an acrylic-based elastomer, or an olefin-based elastomer, or a hard resin such as polysulfon. In this embodiment, the hood member 37 is formed of the soft member.

The hood member 37 has a projecting portion 38 and an endoscope fixing portion 39.

The projecting portion 38 is shaped like a flower petal so as to project frontward in the view from the end portion 17. The endoscope fixing portion 39 is formed at a proximal end of the projecting portion 38 like a cylinder.

The endoscope fixing portion 39 is formed to have an inner diameter that is substantially the same as or slightly smaller than the outer diameter of the end portion 17. The endoscope fixing portion 39 is also formed to be deformable. Thus, the end portion 17 can be press-fitted into the endoscope fixing portion 39.

The endoscope fixing portion 39 is provided with a tapered portion 45 around the outer periphery of its proximal end portion. When the proximal end portion is formed like a low step and is made thin so as to be easily deformed, the tapered portion 45 allows the end portion 17 to be press-fitted into the endoscope fixing portion 39.

The level of clamping for press fitting is set to provide such a fixing strength that the hood member does not slip out in spite of the friction between itself and the wall of the coelom during examinations but can be easily removed after the operation has been completed. Specifically, it is set so that the amount of force required to remove the hood member is about 5 to 20 N.

The endoscope fixing portion 39 has as large a length as possible to the extent that the end of the endoscope fixing portion 39 does not reach the position of a rotationally moving pin 36 located at the tip of the bent portion 16. Thus, the endoscope fixing portion 39 is reliably fixed by maximizing the length over which the endoscope fixing portion 39 is fitted over the end portion 17 to the extent that a bending operation of the bent portion 16 is not affected. An end portion abutting portion 40 is formed between the endoscope fixing portion 39 and the projecting portion 38 so as to project from this position in such a manner that the diameter of the hood member at this position is smaller than the outer diameter of the end portion 17.

The end surface of the end portion 17 abuts against the end portion abutting portion 40 so as to position the end portion 17 and the hood member 37 in an axial direction. The end portion abutting portion 40 need not extend all over the circumference but over only part of it.

As shown in FIG. 3, the end portion abutting portion 40 is partly provided with a rotating direction positioning portion 41 projecting inward.

A concave nozzle engaging groove 42 is cut in the rotating direction positioning portion 41. The air and water supply nozzle 18 engages with the nozzle engaging groove 42 to position the end portion 17 and the hood member 37 in the direction of rotation around the axial direction.

The projecting portion 38 has a conical slope portion 44 formed on its inner peripheral surface and having a diameter increasing from the end portion abutting portion 40 to the end of the projecting portion. Thus, on the inner peripheral surface of the projecting portion 38, water, body fluids, contaminants, and other substances sticking to the surface of the end portion 17 are likely to flow easily to the exterior of the projecting portion 38. That is, the water and other substances are unlikely to remain there.

As shown in FIGS. 3 and 4, an edge portion 43 of the projecting portion 38 is shaped to correspond to an observation view area of the observing optical system 34 so as to minimize the area of that part of the end portion 43 which is viewed in an observed image.

As shown in FIG. 5, an observed image displayed on the monitor 6 is generally shaped like a rectangle.

FIG. 6 shows the observation view area used to display the observed image 46.

A face A1 is a lens face of the tip lens of the observing optical system 34, shown in FIG. 3. A face B1 is a virtual face located about 4 mm frontward from this lens face.

The observation view area on the face A1 is an area a1. The observation view area on the face B1 is an area b1.

The space sandwiched between the area a1 and the area b1 is an observation view area 47.

In this case, a side face of the observation view area 47 is a slope 48 formed of a set of light beams.

As shown in FIG. 5, the length L1 of the observed image 46 in its side-to-side direction is larger than its length L2 in its diagonal direction. Accordingly, the view angle is larger in the diagonal direction.

Further, with the observing optical system 34, typically used for the endoscope 2, owing to possible aberration based on its characteristics, an image is more markedly compressed at a position further from its center.

Thus, in the case of the shape of the observed image 46 shown in FIG. 5, the area b1 does not the same shape as the observed image 46 but is larger than the observed image 46 in the diagonal direction X, as shown in FIG. 6. Thus, the slope 48 has a biased shape.

As shown in FIGS. 2 and 4, the end edge portion 43 is shaped so as to correspond to the slope 48. A slope portion 49 shaped to have substantially the same shape as the slope 48, shown in FIG. 6, is formed on the end edge portion 43, shown in the upper part of FIGS. 2 and 4, and a portion 43a, shown shaded in FIG. 3, at the corresponding positions. Alternatively, as shown in FIGS. 2 and 4, the slope portion 49 is formed at positions slightly offset from the shape of the slope 48.

As shown in FIGS. 3 and 4, the end edge portion 43 is formed to be uneven so as to reflect the shape of the slope 48, described previously. In this case, in the end edge portion 43, portions A, B, C, and D are convex, while portions E, F, G, and H are concave.

If the projecting portion 38 includes a concave and convex portions, its part located near the observing optical system 34 is desirably shaped as a convex portion so as to have a larger projecting length. It is desirable to have at least three convex portions.

The portions E, F, G, and H, which are concave, are open outward because the slope portion 44 is connected to the slope 48. Mucus, contaminants, water supplied through the air and water supply nozzle, and the like are discharged from these concave portions to the exterior of the projecting portion 38 via the slope portion 44. This prevents contaminants, mucus, or the like from blocking the view.

As shown in FIG. 4, the end edge portion 43 has a chamfer 71 of R about 0.3 to 1 mm formed at its outer peripheral edge. The slope portion 49 also has a chamber of R about 0.3 to 1 mm formed at its end.

As shown in FIG. 2, the observing optical system 34 has an observation depth set between 4 and 100 mm. Further, the amount of projection L0 of the end edge portion 43 at the position at which it projects furthest from the tip lens of the observing optical system 34 is set to be substantially equal to or larger than the minimum value (near point) of this depth. In this embodiment, the end edge portion 43 is formed to project so that the amount of projection L0 is about 4 mm.

With this structure, the endoscope apparatus 1 of this embodiment is provided with the hood member 37 having the projecting portion 38 which is provided at the end portion 17 of the inserted portion 7 of the endoscope 2 and which projects in the direction of the observation view of the endoscope 2. The observed image 46, obtained through the endoscope 2, is not circular.

Further, in the endoscope apparatus 1, the projecting portion 38 has the slope portion 49 formed at its end edge potion 43 so as to correspond to the observation view area 47 of the endoscope 2.

If the hood member is transparent, it does not block illumination light. This results in high illumination performance.

The hood member may be black. In this case, the projecting portion may be aligned with the observation view area 47 of the endoscope 2. Further, like the previously described observing view are, the projecting portion may be provided with a notch and a slope portion.

If the hood member is black, illumination light is not reflected by the inner wall of the hood member. This prevents halation, which may occur when the treatment instrument is used.

Further, endoscopes applicable to the hood member may have the same color as the hood member, whereas endoscopes not applicable to the hood member may have a different color. Further, to allow the hood member to be easily removed from the end portion, the hood member and the end member may have different colors so as to be easily distinguished from each other.

The hood member may have the types of applicable endoscopes or the outer diameters of the end portions of these endoscopes indicated thereon.

The amount of projection of the projecting portion may be set between about 2 and 10 mm.

Figure 7:
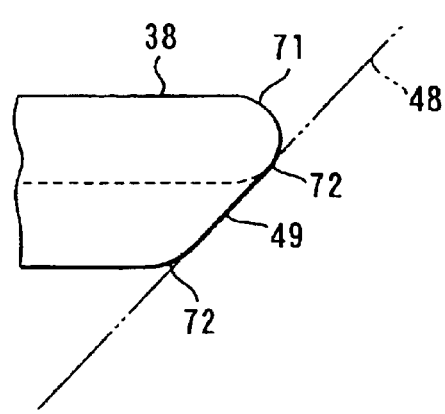
FIG. 7 is a first view illustrating effects of a projecting portion according to the first embodiment of the present invention.
Figure 8:
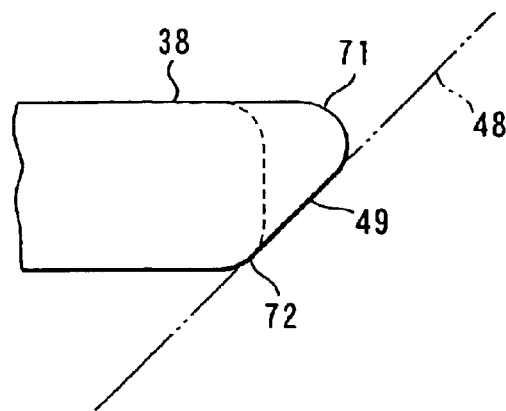
FIG. 8 is a second view illustrating effects of the projecting portion according to the first embodiment of the present invention.

FIGS. 7 and 8 are views illustrating effects of the projecting portion 38 according to the first embodiment. In FIG. 7, the solid line indicates the shape of the projecting portion 38 according to this embodiment. The broken line indicates the shape of the projecting portion 38 obtained if chamfers 71 and 72 are formed with the projecting length of the projecting portion 38 maintained and without providing the slope portion 49. If the projecting portion 38 is formed as shown by the broken line, the projecting portion 38 is thinner.

That is, in this embodiment, the slope portion 49 is formed to correspond to the observation view area 48, thereby increasing the thickness of the projecting portion 38 without reducing the projecting length of the projecting member 38. Thus, this embodiment makes the projecting portion 38 difficult to damage and prevents the projecting portion 38 from being deformed when pressed against the inner wall of the coelom even when it has a plurality of notches. Further, in this embodiment, the chamfers 71 and 72 may be formed to be large to allow the end portion to be easily inserted.

In FIG. 8, the solid line indicates the shape of the projecting portion 38 according to this embodiment. Further, the broken line indicates the shape of the projecting portion 38 obtained if it does not have the slope portion 49 formed thereon so as to have an adequate thickness. If the projecting portion 38 is formed as shown by the broken line, it has an insufficient projecting length.

That is, this embodiment enables the projecting length of the projecting portion 38 to be increased without increasing its outer diameter. This helps to improve the performance of the hood.

Further, even if the mucous membrane abuts against the end edge portion 43 to cover the entire view, the observing optical system 34 is focused on the mucous membrane on the end edge portion 43 by setting the amount of projection L0 of the end edge portion 43, shown in FIG. 2, to be larger than the value for the near point of the observation depth of the observing optical system 34. This makes the observed image clearer.

As described above, according to this embodiment, an endoscope apparatus can be provided which has a small diameter and in which the hood member 37 is difficult to damage, the endoscope apparatus allowing the ending end portion to be easily inserted into the hood member and serving to reduce the area of that part of the hood member 37 which is viewed in the observed image, thereby achieving high observation performance. Further, according to this embodiment, an endoscope apparatus is provided which exhibits high observation performance even if the hood member 37 abuts against the mucous membrane.

In the embodiment shown in FIGS. 1 to 6, an index used to position the hood member 37 in the rotating direction may be provided, for example, at the end edge potion 43 rather than forming the nozzle engaging groove 42. In this case, an index may be provided at the end portion 17, which is aligned with the index of the end edge portion 43, or the air and water supply nozzle 18, suction port 19, or observing optical system 34 of the end portion 17 may be aligned therewith.

If the hood member 37 is separate from the endoscope 2, the mounting position of the hood member 37 and the viewing of the observed image are likely to vary. However, a large protruding length is ensured in spite of such a variation by providing a slope portion corresponding to the observation view area at the respective positions to form as large a protruding length as possible.

Further, according to this embodiment, the hood member 37 can be easily mounted by providing positioning means for the axial or rotating direction or indices to arrange the slope portion at the appropriate position for the observation view area.

Second Embodiment

Figure 9:
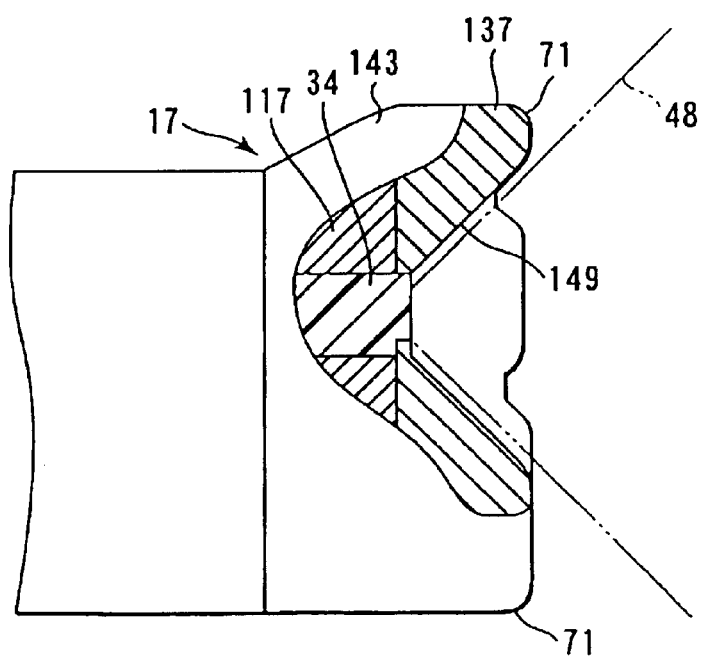
FIG. 9 is a partly cutaway side view of an end portion of an endoscope according to a second embodiment of the present invention.

FIG. 9 is a partly cutaway side view of an end portion of an endoscope according to a second embodiment of the present invention.

The second embodiment shown in FIG. 9 differs from the first embodiment in that a hood member 137 is integrated with the end portion 17.

As shown in FIG. 9, the hood member 137 is formed of a hard resin such as polysulfon and also acts as an insulating cover that covers a metal part inside the end portion 17.

The observing optical system 34 of the end portion 17 has an observation view area 47 similar to that in the first embodiment, shown in FIG. 6.

An end edge portion 143 of the hood member 137 has slope portions 149 formed at the respective positions and corresponding to the slope 48 of the observation view area 47.

The slope portion 149 is formed in the end edge portion 143 of the hood member 137 and corresponds to the slope 48 of the observation view area 47 at the respective positions as in the case with the first embodiment, shown in FIGS. 1 to 6.

Further, the end edge portion 143 has the chamfer 71 of R about 1 mm formed at its outer peripheral edge.

In this embodiment, the slope portion is formed to be as wide as possible, and the end edge portion 143 is formed to be as thick as possible.

If the hood member 137 and the end portion 17 are integrated together, a hard member is more durable than a soft member in terms of tearing and wearing.

If the hood member 137 is formed of a hard member, the end edge portion 143 is easier to damage when undergoing impact or the like compared to a soft member. However, in the second embodiment, the end edge portion 143 can be formed to be thick and the chamfer 71 can be formed to be markedly curved, thereby making the end edge portion 143 sufficiently difficult to damage even if the hood member 137 is hard.

Third Embodiment

Figure 10:
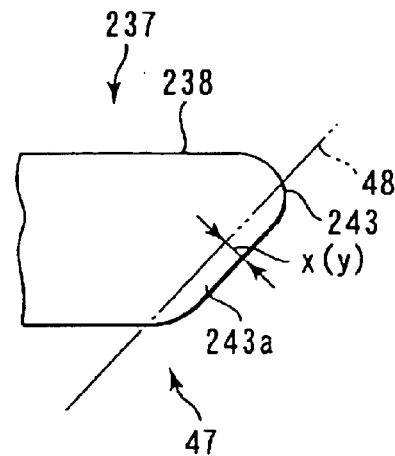
FIG. 10 is a side view showing a projecting portion of an end portion of an endoscope according to a third embodiment of the present invention.
Figure 11:
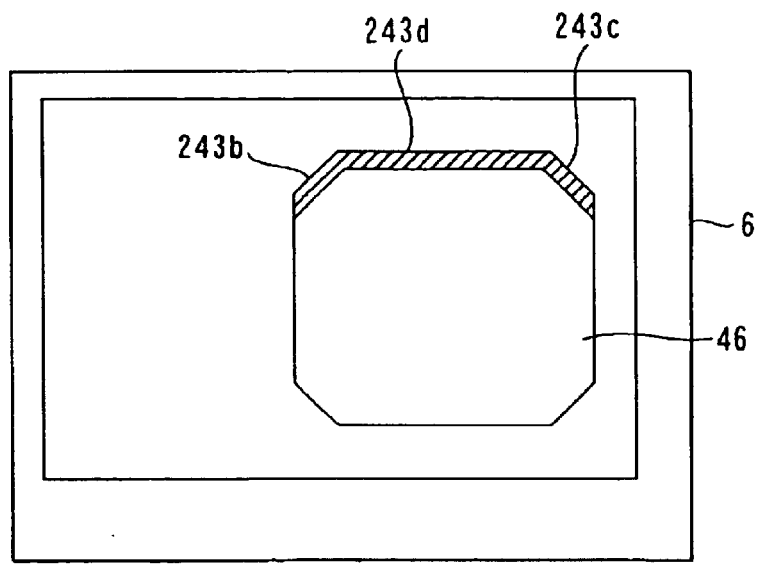
FIG. 11 a plan view showing an observed image displayed on a monitor according to the third embodiment of the present invention.

FIGS. 10 and 11 relate to a third embodiment of the present invention. FIG. 10 is a side view showing a protruding portion of the endoscope. FIG. 11 is a plan view showing an observed image displayed on a monitor.

As shown in FIG. 10, a protruding portion 238 of a hood member 237 provided at an end portion of the endoscope of this embodiment has a portion 243a formed so that a very small part of the end portion of the end edge portion 243 overlaps the slope 48 of the observation view area 47. That is, the portion 243a extends into the observation view area 47.

The amount of overlapping x by which the end edge portion 243 overlaps the observation view area 47 at positions distant from the center of the observation view area in the diagonal direction X shown in FIG. 6 is larger than the amount of overlapping y at other positions. That is, as shown in FIG. 11, considering aberration in the observing optical system 34, the amounts of overlapping x and y are set so that the area of that part of the end edge portion which is viewed on the observed image 46 is uniform.

In this embodiment, aberration in the observing optical system 34 causes the image to be most significantly compressed at positions distant from the center of the observation view area in the diagonal direction X shown in FIG. 6. Thus, as shown in FIG. 11, in the observed image 46 on the monitor 6, images 243b and 243c of the end edge portion 243 are compressed which project outward from the slope 48 in the diagonal direction X to overlap the observation view area 47. Thus, the images 243b and 243c of the end edge portion 243 are viewed on the observed image in substantially the same manner as an image 243d of the end edge portion 243 that overlaps the observation view area at other positions.

Thus, the protruding length or thickness of the hood member 237 can be formed to be large while minimizing the adverse effects on the observation view.

As described above, this embodiment produces effects similar to those of the embodiment shown in FIGS. 1 to 6. Furthermore, this embodiment provides an endoscope apparatus that allows the hood member 237 to be formed to have a large protruding length or thickness to allow the end portion to be easily inserted into the hood member or improve durability.

Fourth Embodiment

Figure 12:
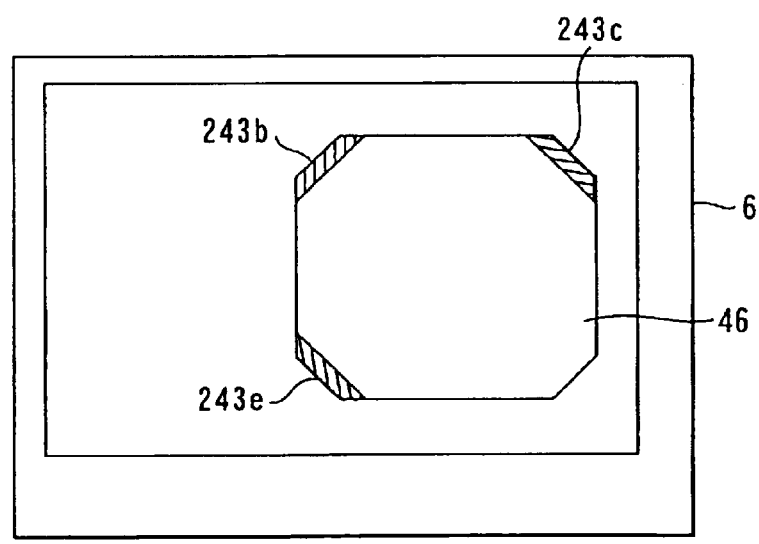
FIG. 12 a plan view showing an observed image displayed on a monitor of an endoscope apparatus according to a fourth embodiment of the present invention.

FIG. 12 is a plan view showing an observed image displayed on the monitor according to a fourth embodiment of the present invention. With reference to FIG. 10, description will be give of the shape of a protruding portion of an end portion of an endoscope according to the fourth embodiment.

This embodiment has a portion in which the end portion of the end edge portion 243 overlaps the slope 48 of the observation view area 47, shown in FIG. 10, by a very small amount only at positions distant from the center of the observation view area in the diagonal direction X. Thus, as shown in FIG. 12, the observed image 46 on the monitor 6 shows images 243b, 243c, and 243e of the end edge portion 243 which project outward from the slope 48 in the diagonal direction X to overlap the observation view area 47.

In this embodiment, that part of the view in the diagonal direction X which is significantly compressed and which has a large angle of view has a slightly reduced size in the observed image 46 on the monitor 6. However, the hood member 237 can be formed to have a large protruding length or thickness without further reducing the size of that part of the view which is insignificantly compressed and which originally has a small angle of view.

As described above, the fourth embodiment produces effects similar to those of the third embodiment, shown in FIGS. 10 and 11. Furthermore, the fourth embodiment provides an endoscope apparatus that exhibits high observation performance.

The first to fourth embodiments are applicable to endoscopes having circular observed images such as those shown in FIGS. 13, 14, 15, and 16.

Figure 13:
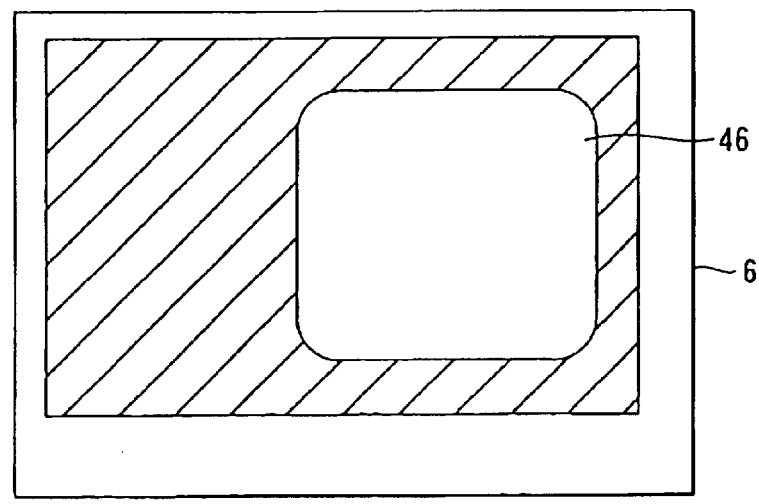
FIG. 13 is a plan view showing a first example of a non-circular observed image that can be used in the first to fourth embodiments.
Figure 14:
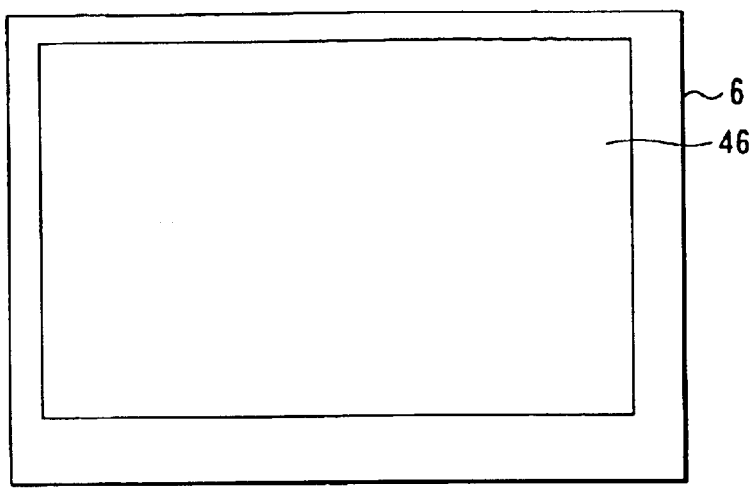
FIG. 14 is a plan view showing a second example of a non-circular observed image that can be used in the first to fourth embodiments.
Figure 15:
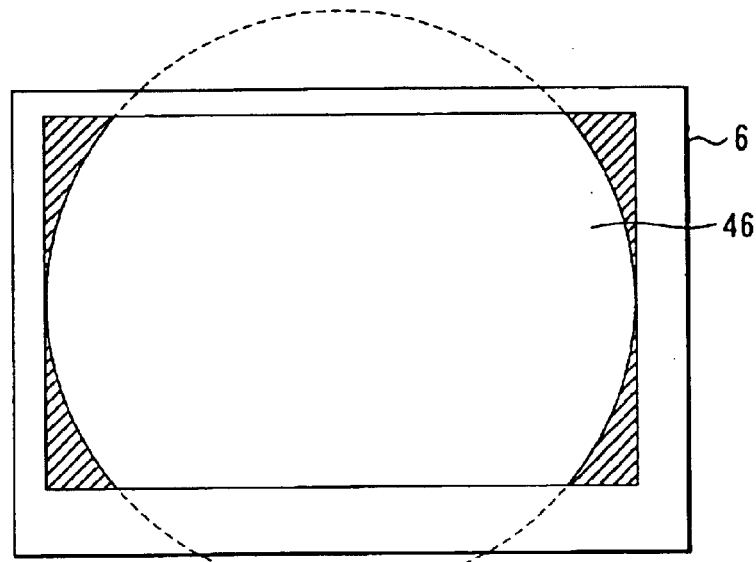
FIG. 15 is a plan view showing a third example of a non-circular observed image that can be used in the first to fourth embodiments.
Figure 16:
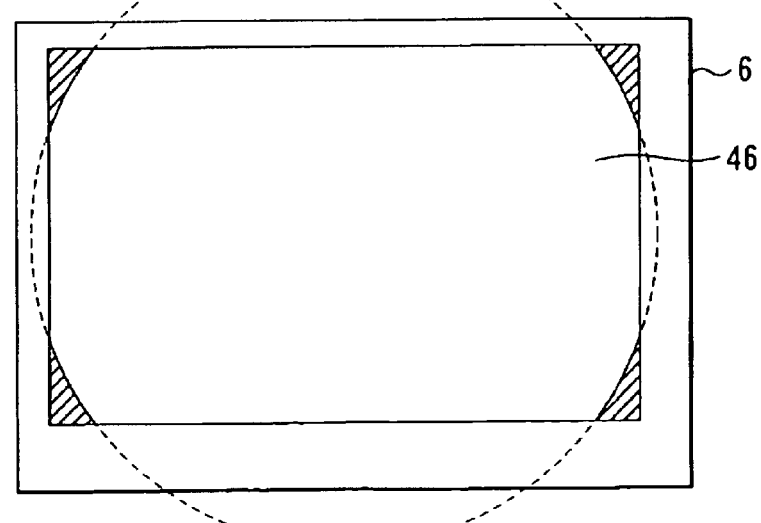
FIG. 16 is a plan view showing a fourth example of a non-circular observed image that can be used in the first to fourth embodiments.

In FIG. 13, the observed image 46 is a general square or rectangle with rounded corners. In FIG. 14, the observed image 46 is a rectangle displayed all over the screen of the monitor 6. In FIG. 15, the observed image 16 is a general rectangle obtained by cutting out the top and bottom of a circle. In FIG. 16, the observed image 16 is a general rectangle obtained by cutting out the top, bottom, and rightmost and leftmost portions of a circle.

Fifth Embodiment

Figure 17:
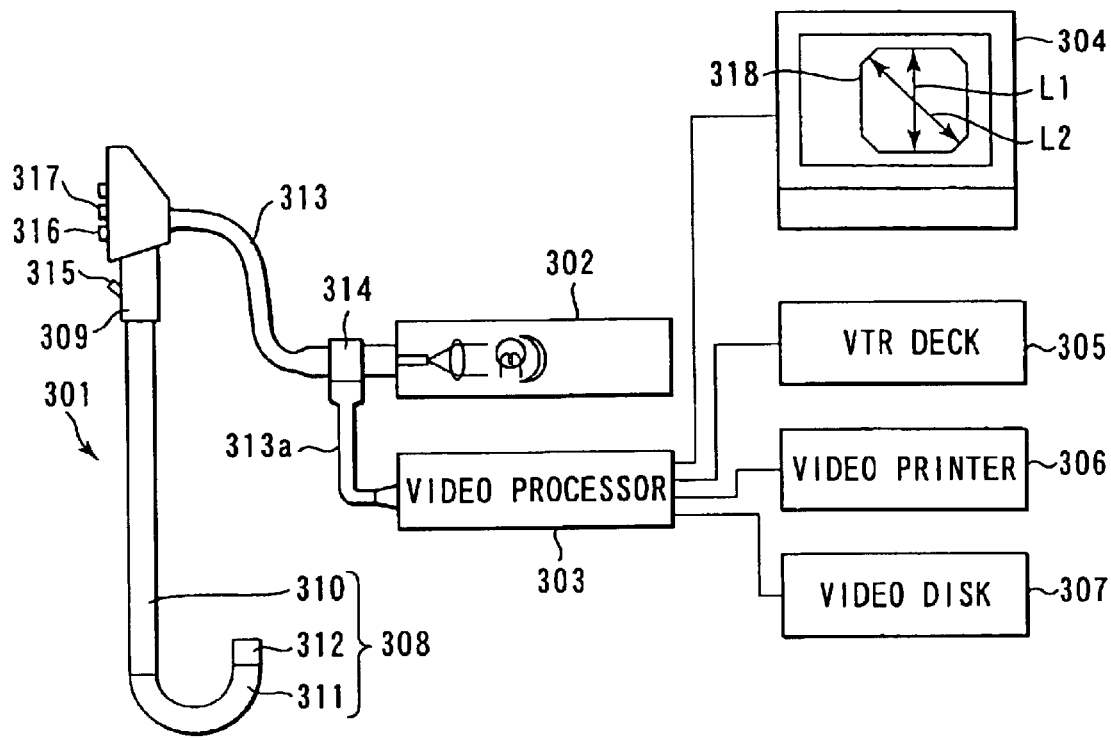
FIG. 17 is a view schematically showing the configuration of an entire endoscope apparatus according to a fifth embodiment of the present invention.

A fifth embodiment will be described with reference to FIGS. 17 to 21. FIG. 17 schematically shows the entire configuration of an endoscope apparatus. The endoscope apparatus is composed of an endoscope 301, a light source device 302, a video processor 303 having a video signal processing circuit and a drive circuit built thereinto, and peripheral equipment such as a monitor 4 connected to the video processor 303, a VTR deck 5, a video printer 6, and a video disk 7.

The endoscope 301 comprises an inserted portion 308 inserted into the coelom, a manipulating section 309 connected to a proximal end of the inserted portion 308, and a universal cord 313 extended from the manipulating section 309. The universal cord 313 extended from the manipulating section 309 is provided with a connector 314 at its end. The connector 314 is connected to the light source device 302. Further, the connector 314 and the video processor 303 are connected together via a connection cord 313a.

The inserted portion 308 is composed of a soft portion 310, a bent portion 311 connected to the soft portion 310, and an end portion 312 connected to the bent portion 311.

The manipulating portion 309 is provided with a forceps port 315, an air and water supply switch 316, a suction switch 317, and a knob for upward, downward, rightward, and leftward bending operations (not shown). The bending operation knob can be operated to bend the bent portion 311 to manipulate the direction of the end portion 312.

An observed image 318 of the endoscope 301 displayed on the monitor 304 is generally rectangular. The side-to-side direction of the general rectangle of the observed image 318 is defined as L1. The diagonal direction of the general rectangle is defined as L2.

Figure 18:
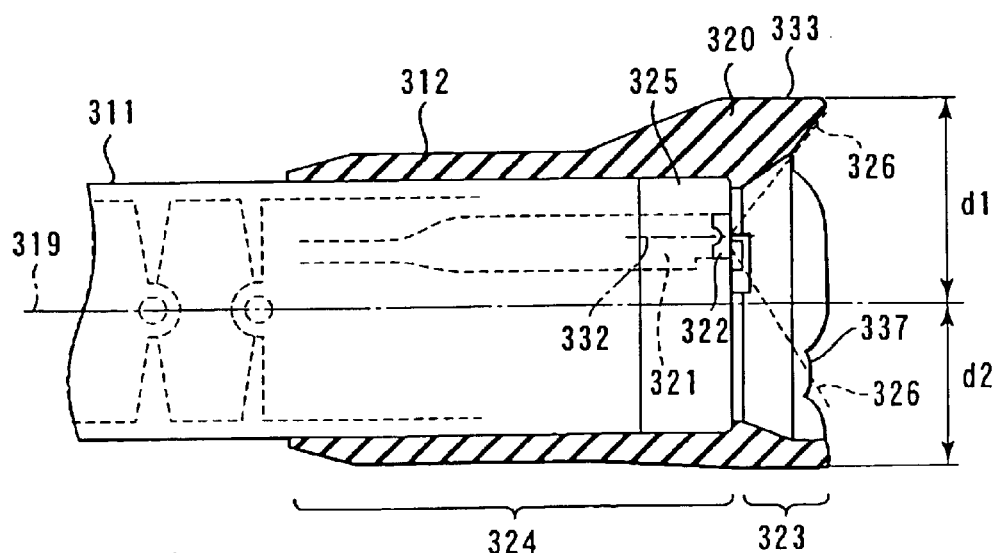
FIG. 18 is a vertical sectional view of an end portion of an endoscope according to the fifth embodiment.

FIG. 18 shows a vertical section taken near the end portion of the endoscope 301.

The end portion 312 is provided with a hood portion 320. The hood portion 320 forms a projecting portion 323 that projects further frontward from an end surface of an objective lens 322 of an objective optical system unit 321. An end edge of the projecting portion 323 of the hood portion 320 is formed so as not to enter an observation view area 326, shown by the broken line in the figure.

The hood portion 320 can be freely installed on and removed from the end portion 312. A fitted portion 324 for the end portion 312 is provided so that the hood portion 320 is press-fitted into the fitted portion 324. A part of the outer periphery of the projecting portion 323 of the hood portion 320 is located at a distance from an axis of the inserted portion 308 which distance is different from that to the other parts as shown by distances d1 and d2 (d1>d2). This forms an outer peripheral portion 333 that protrudes in the direction d1.

FIG. 19 shows the end portion 312 of the endoscope 301 as viewed from the front of the end.

The end portion 312 is provided with the objective lens 322, an illuminating lens 327, a forceps channel opening 328, and an air and water supply nozzle 329 as common components of the end portion of the endoscope.

A convex portion 330 and a concave portion 331 are formed around the air and water nozzle 329 as a part of the hood portion 320. These portions allow the hood portion 320 to be mounted on the end portion 312 in the correct rotating direction. If the hood portion is correctly mounted on the end portion, the air and water supply nozzle 329 can be fitted and inserted into the concave portion 331 as shown in FIG. 19.

The objective optical system unit 321, i.e. an optical axis 332 of the objective lens 322 does not coincide with an axis 319 of the inserted portion 308 but deviates therefrom. This is because in arranging the objective lens 322, the illuminating lens 327, the forceps channel opening 328, the air and water supply nozzle, and others, the optical axis 332 must be arranged so as to deviate from the axis 319 of the inserted portion 308 in order to minimize the outer diameter of the end portion 312 because the forceps channel opening 328 has a particularly large diameter.

This arrangement of the optical axis 332 corresponds to the deviation of the optical axis 332 from the axis 319 of the inserted portion 308 in a substantially upward direction. The upward direction is such that when the operator manipulates the manipulating section 309 to bend the bent portion 311 upward, the observed image 318 on the monitor 304 moves upward.

Further, the outer peripheral portion 333 of the projecting portion 323 of the hood portion 320 is formed to protrude in the upward direction as shown by d1. The direction in which the outer peripheral portion 333 protrudes is substantially the same as the direction in which the optical axis 332 deviates from the axis 319 of the inserted portion 308.

FIG. 20 shows how the end of the projecting portion 323 of the hood portion 320 of the end portion 312 abuts against a wall 334 of a living body.

Since the projecting portion 323 abuts against the living body wall 334, the end surface of the objective lens 322 does not abut against the living body wall 334 but maintains a distance therefrom which corresponds to the projecting height h1 of the projecting portion 323.

The projecting portion 323 need not necessarily have the projecting height h1 all over its circumference but at least at two points. These two points abut against the living body wall 334 to keep the distance from the end surface of the objective lens 322 to the living body wall 334 equal to the projecting height h1 as shown in FIG. 20.

In this case, the projecting height is most desirably within the range of an observation depth. If for example, the objective optical system unit 321 has an observation depth of 5 to 100 mm, then the projecting height h1 is most desirably at least 5 mm and at most 100 mm. If the projecting height h1 is 4 mm, a point 335 on the living body wall 334 which is located substantially on the optical axis 332 is out of the observation depth range. However, preferably, a certain part of the living body wall 334 which is not on the optical axis 332 in the observation view area 326, e.g. a point 336 on the living body wall 334 which is closer to an end of the observation view area 326 is located at least 5 mm away from the end surface of the objective lens 322, and in this state, a certain part of the observed image 318 can be focused. That is, the projecting portion 323 has, in a plurality of parts, such a projecting height that at least part of the observed image 318 can be focused when the projecting portion 323 is abutted against the living body wall 334.

The projecting portion 323 desirably has a sufficient projecting height in as many parts of it as possible, and more desirably all over its circumference. In this embodiment, the projecting portion 323 does not have a uniform projecting height all over its circumference but is partly provided with a concave portion 337 as shown in FIG. 18.

In this embodiment, the outer peripheral portion 333 of the hood portion 320 is protruded in substantially the same direction as that in which the optical axis 332 deviates from the axis 319 of the inserted portion 308, and the end portion 312 is located at a sufficient distance from the axis 319 of the inserted portion 308. Consequently, the outer peripheral portion 333 has a sufficient forward protruding height, and the hood portion 320 is hindered from entering the observation view area 326.

Further, the outer peripheral portion 333 of the hood portion 320 affects the size of the outer diameter of the end portion 312. However, since the hood portion 320 only partly has an increased radius with respect to the axis 319 of the inserted portion 308, such adverse effects can be minimized.

FIG. 21 shows the observation view area 326 as viewed from the front of the apparatus.

First, as shown by the broken line in the figure, an observation view area 326a has a shape close to that of the observed image 318 viewed on the monitor 304 provided on the end surface of the objective lens 322. However, at a certain distance from the end surface of the objective lens 322, the observation view area is widened in an area corresponding to a diagonal direction L2 as shown at 326b in the figure. This is because owing to aberration in the objective optical system unit, an image is more markedly compressed at a position further from its center. Accordingly, if the observed image 318 is not a circle, the angle of the observation view area 26 (view angle) shown in FIGS. 18 and 20 is larger in the diagonal direction L2 than in the side-to-side direction L1.

In FIGS. 18 and 20, the observation view area 326 indicates upward and downward directions and thus the side-to-side direction L1. However, the observation view area 326 is wider in the diagonal direction L2, not shown in FIGS. 18 and 20, than in the side-to-side direction L1. Accordingly, the projecting height of the hood portion 320 corresponding to the diagonal direction L2 of the observation view area 326 is slightly reduced as with the concave portion 337 in FIG. 18. This minimizes the area of that part of the hood portion 320 which is viewed in the observed image 318.

Further, for the same reason, the optical axis 332 deviates from the axis 319 of the inserted portion 308 in the side-to-side direction L1 (in this embodiment, the upward direction). That is, this ensures a sufficient projecting height while minimizing the length over which the outer peripheral portion 333 protrudes in the outer peripheral direction, thus minimizing the area of that part of the hood portion 320 which is viewed in the observation view area 326.

For example, it is assumed that at least two points of the hood portion 320 comes into contact with the living body wall 34 as shown in FIG. 20. Then, provided that at least part of the observed image is within the observation depth range, i.e. at least part of it is focused, the image does not become deeply red in that part but shows the living mucus of the living body wall 334. Consequently, the operator is prevented from being confused, and if the treatment instrument has been inserted, can easily determine the direction in the lumen in which the instrument advances subsequently. On the other hand, while observing a lesion, the operator can easily view this lesion.

Further, since the hood portion 320 can be freely installed on and removed from the end portion 312, the hood portion 320 can be removed from the end portion 312 if the operator desires to reduce the outer diameter of the endoscope for a treatment or in cases requiring such a reduction.

According to the fifth embodiment, the projecting height can be maximized to the extent that the hood portion 320 as a whole does not interfere with observations, i.e. does not markedly block the observation view area. This hinders the viewing range from being narrowed to allow the hood portion 320 to exhibit sufficient performance.

In the fifth embodiment, the hood portion 320 can be freely installed on and removed from the end portion 312. However, the hood portion 320 may be fixed so as not to be removed from the end portion 312. If the hood portion is thus fixed so as not to be removed from the end portion 312, the projecting portion 323 is molded so as to be integrated with a resin cover 325. When the hood portion 320 is thus fixed, it is unnecessary to install or remove the hood portion 320. Therefore, although the hood portion 320 has a slightly increased outer diameter, an endoscope is provided which is very convenient for users who focus on the effects of the hood portion 320.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
an endoscope comprising an observing device which has an observation view area, the observing device displaying the observation view area as a non-circular observed image; and
a hood member mounted on an end of an inserted section of the endoscope and comprising a hood section which projects in the direction of the observation view area and provided integrally with the inserted section of the endoscope or freely detachable therefrom, at least a part of the hood member having a slope that is shaped at a thick portion of the hood section so as to correspond to the observation view area.

2. The endoscope apparatus according to claim 1, wherein the observing device includes an image pickup section and an objective optical system.

3. The endoscope apparatus according to claim 2, wherein the image pickup section includes an image pickup element, and the observed image picked up by the image pickup element has a non-circular shape.

4. The endoscope apparatus according to claim 2, wherein the endoscope apparatus further includes a monitor which displays the observed image from the observing device, and a display area of the monitor for the observed image has a non-circular shape.

5. An endoscope hood member comprising:

a hood section projecting in a direction of an observation view area of an endoscope; and a slope provided at a thick portion of the hood section and shaved to correspond to the observation view area of the endoscope displaying an observed image as a non-circular observed image, wherein the hood section is provided to be integral with an inserted section of the endoscope or freely detachable therefrom.

6. The endoscope hood member according to claim 5, wherein the hood section has at least one notch section.

7. An endoscope hood member comprising:

a mounted section mounted on an end of an inserted section of an endoscope which provides a non-circular observed image; and a hood member mounted on the end of the inserted section and having a hood section extending in the direction of an observation view area of the endoscope, at least a part of the hood section being provided with a sloped section corresponding to the observation view area, wherein the amount of that part of the hood section which overlaps the observation view area within at least a part of the range of positions distant from a center of the observed image is formed to be larger than the amount of that part of the hood section which overlaps the observing view area within the other ranges.

8. The endoscope hood member according to claim 7, wherein the observed image is generally rectangular, and the amount of that part of the hood section which overlaps the observation view area within the range of positions near at least one corner of the observed image is formed to be larger than the amount of that part of the hood section which overlaps the observation view area within the range of positions near sides of the observed image.

9. The endoscope hood member according to claim 8, wherein the hood section is shaped so as to be contained in the observation view area within the range of positions near at least one corer of the observed image but not within the range of positions near sides of the observed image.

10. An endoscope hood member comprising:

a mounted section mounted on an end of an inserted section of an endoscope which provides a non-circular observed image; and a hood member mounted on the end of the inserted section and having a hood section extending in the direction of an observation view area of the endoscope, at least a part of the hood section being provided with a sloped section corresponding to the observation view area, wherein the maximum length of that part of the hood section which projects from a tip lens surface of the observing optical system is formed to be larger than a minimum observation depth of the observing optical system.

11. An endoscope apparatus comprising:

an endoscope which has an inserted section provided with an objective optical system at an end of the inserted section, the objective optical system having an observation view area;

an observed image display device which displays an image of the observation view area of the objective optical system as an observed image; and a hood member mounted on the end of the inserted section of the endoscope and having a hood section which extends in the direction of the observation view area and is provided integrally with the inserted section of the endoscope or freely detachable therefrom, at least a part of the hood member being provided with a slope section that is shaped at a thick portion of the hood section so as to correspond to the observation view area.

12. The endoscope apparatus according to claim 11, wherein the observed image display device includes an image pickup element which picks up an image of the observation view area obtained by the objective optical system, and a monitor which displays the observed image picked up by the image pickup element.

13. The endoscope apparatus according to claim 12, wherein at least one of the display areas of the image pickup element and monitor in which areas the observed image is displayed is not circular.

14. The endoscope apparatus according to claim 11, wherein the hood section has at least one notch section.

15. An endoscope apparatus comprising:

an endoscope which has an inserted section provided with an objective optical system at an end of the inserted section, the objective optical system having an observation view area;

an observed image display device which displays an image of the observation view area of the objective optical system as an observed image; and a hood member mounted on the end of the inserted section and having a hood section which extends in the direction of the observation view area, at least a part of the hood member being provided with a sloped section that is shaped so as to correspond the observation view area, wherein the amount of that part of the hood section which overlaps the observation view area within at least a part of the range of positions distant from a center of the observed image is formed to be larger than the amount of that part of the hood section which overlaps the observation view area within the other ranges.

16. The endoscope apparatus according to claim 15, wherein the observed image is generally rectangular, and the amount of that part of the hood section which overlaps the observation view area within the range of positions near at least one corner of the observed image is formed to be larger than the amount of that part of the hood section which overlaps the observation view area within the range of positions near sides of the observed image.

17. The endoscope apparatus according to claim 16, wherein the hood section is shaped so as to be contained in the observation view area within the range of positions near at least one corner of the observed image but not within the range of positions near sides of the observed image.

18. An endoscope apparatus comprising:

an endoscope which has an inserted section provided with an objective optical system at an end of the inserted section, the objective optical system having an observation view area;

an observed image display device which displays an image of the observation view area of the objective optical system as an observed image; and a hood member mounted on the end of the inserted section and having a hood section which extends in the direction of the observation view area, at least a part of the hood member being provided with a sloped section that is shaped so as to correspond the observation view area, wherein the maximum length of that part of the hood section which projects from a tip lens surface of the observing optical system is formed to be larger than a minimum observation depth of the observing optical system.

19. The endoscope apparatus according to claim 11, wherein the hood member is formed so as to be freely installed on and removed from the end section of the endoscope, and is provided with a positioning section which carries out positioning for installation and removal.

20. The endoscope apparatus according to claim 11, wherein the hood member is formed so as to be freely installed on and removed from the end section of the endoscope, and is provided with an index indicative of a position at which the end section and the hood member are fixed together.

21. An endoscope hood member comprising:
a hood section protecting in a direction of an observation view area by an objective optical system of an endoscope,
wherein an outer peripheral portion of the hood section, projecting in a direction in which an optical axis of the objective optical system is arranged with respect to an axis of an elongated inserted section of the endoscope including the objective optical system for observation of an object, is arranged to project further than other portions and
the hood section is provided integrally with the inserted section of the endoscope or freely detachable therefrom.

22. An endoscope hood member comprising:
a mounted section mounted on an end of an endoscope inserted section which includes an objective optical system having an optical axis offset from an axis of the endoscope inserted section; and
a hood section, which is formed on the mounted section, the outer periphery of which projects further in a direction in which the optical axis of the objective optical system is arranged with respect to the axis of the endoscope inserted section, than in the other directions, wherein the projection of the outer periphery of the hood section is arranged in substantially the same direction as an upward direction of the inserted section.

23. An endoscope hood member comprising:
a mounted section mounted on an end of an endoscope inserted section which includes an objective optical system having an optical axis offset from an axis of the endoscope inserted section; and
a hood section, which is formed on the mounted section, the outer periphery of which projects further in a direction in which the optical axis of the objective optical system is arranged with respect to the axis of the endoscope inserted section, than in the other directions, wherein the hood section has a substantially elliptic cross section.

24. The endoscope hood member according to claim 23, wherein the hood section is formed of a plurality of projecting sections projecting from the mounted section toward the end of the inserted section.

25. The endoscope hood member according to claim 24, wherein at least two of the plurality of projecting sections have the same length.

26. The endoscope hood member according to claim 24, wherein the length of the projecting section is substantially equal to or larger than a near point of an observation depth.

27. An endoscope apparatus comprising:
an endoscope which includes an inserted section having an axis;
an objective optical system provided in the inserted section and having an optical axis arranged offset from the axis of the inserted section, and
a hood member which includes a hood section projecting in an observation view area by the objective optical system and is provided integrally with the inserted section of the endoscope or freely detachable therefrom,
wherein an outer peripheral portion of the hood section, in a direction in which an optical axis of the objective optical system is arranged with respect to an axis of the inserted section, is arranged to further project than other portions.

28. An endoscope apparatus comprising:
an endoscope which includes an inserted section having an axis;
an objective optical system provided in the inserted section and having an optical axis arranged offset from the axis of the inserted section; and
a hood member provided on an end portion of the inserted section and having a mounted section and a hood section the outer periphery of which projects further in a direction in which the optical axis of the objective optical system is arranged with respect to the axis of the endoscope inserted section than in the other directions, wherein the hood section has a generally elliptic cross section.

29. The endoscope apparatus according to claim 28, wherein deviation of the optical axis of the objective optical system from the axis of the inserted section is in substantially the same direction as an upward direction of the inserted section.

30. The endoscope apparatus according to claim 29, wherein the hood section is formed of a plurality of projecting sections projecting from the mounted section toward the end of the inserted section.

31. The endoscope apparatus according to claim 30, wherein at least two of the plurality of projecting sections have the same length.

32. The endoscope apparatus according to claim 31, wherein the length of the projecting section is substantially equal to or larger than a near point of an observation depth.

33. An endoscope apparatus comprising:
an endoscope which has an inserted section having an axis;
an objective optical system provided in the inserted section and having an optical axis arranged offset from the axis of the inserted section; and
a hood member provided on an end portion of the inserted section and having a substantially circular cross section, wherein the length up to the outer periphery of the hood member is set to be shorter in a direction substantially opposite to a direction in which the optical axis of the objective optical system is arranged with respect to the axis of the endoscope inserted section than in substantially the same direction as that in which the optical axis of the objective optical system is arranged, and
the hood member is provided integrally with the inserted section of the endoscope or freely detachable therefrom.

34. An endoscope apparatus comprising:
an endoscope which has an inserted section having an axis;
an objective optical system provided in the inserted section and having an optical axis arranged offset from the axis of the inserted section; and a hood member provided on an end portion of the inserted section and having a substantially circular cross section, wherein the length measured to the outer periphery of the hood member is set to be shorter in a direction substantially opposite to a direction in which the optical axis of the objective optical system is arranged with respect to the axis of the endoscope inserted section than in substantially the same direction as that in which the optical axis of the objective optical system is arranged, wherein deviation of the optical axis of the objective optical system from the axis of the inserted section is in substantially the same direction as an upward direction of the inserted section.

35. The endoscope apparatus according to claim 33, wherein the hood member has a substantially elliptic cross section.

* * * * *